United States Patent [19]

Lahr

[11] Patent Number: 5,713,919
[45] Date of Patent: Feb. 3, 1998

[54] FINGERLIKE MEDICAL INSTRUMENTS FOR USE IN LAPAROSCOPIC PROCEDURES

[76] Inventor: Christopher J. Lahr, 921 Cottonhouse Dr., Charleston, S.C. 29412

[21] Appl. No.: 685,549

[22] Filed: Jul. 24, 1996

Related U.S. Application Data

[62] Division of Ser. No. 434,944, May 4, 1995.

[51] Int. Cl.$^6$ ............................................. A61B 17/28
[52] U.S. Cl. ........................................ 606/207; 606/205
[58] Field of Search ................................. 606/205, 206, 606/207, 170; 128/751, 749, 752, 754

[56] References Cited

U.S. PATENT DOCUMENTS

| | | | |
|---|---|---|---|
| 2,685,880 | 8/1954 | Curutchet | 128/321 |
| 5,002,561 | 3/1991 | Fisher | 606/210 |
| 5,176,696 | 1/1993 | Saunders | 606/174 |
| 5,176,700 | 1/1993 | Brown et al. | 606/206 |
| 5,209,747 | 5/1993 | Knoepfler | 606/16 |
| 5,211,655 | 5/1993 | Hasson | 606/205 |
| 5,275,614 | 1/1994 | Haber et al. | 606/207 |
| 5,304,203 | 4/1994 | El-Mallawany et al. | 606/207 |
| 5,308,357 | 5/1994 | Lichtman | 606/205 |
| 5,441,494 | 8/1995 | Ortiz | 606/205 |
| 5,549,636 | 8/1996 | Li | 606/207 |

*Primary Examiner*—Michael Buiz
*Assistant Examiner*—Kevin Truong
*Attorney, Agent, or Firm*—Senniger, Powers, Leavitt & Roedel

[57] ABSTRACT

A medical instrument for use in a laparoscopy comprises a long, slender body having opposite ends which are distal and proximal relative to a person holding the instrument, a pair of tips adjacent the distal end of the body, at least one of said pair of tips being movable with respect to the other of said tips, and a tip actuation mechanism movably connected at the proximal end of the body for actuating movement of the at least one movable tip. The tip actuation mechanism is longitudinally aligned with the pair of tips and coplanar therewith whereby operator-controlled motion of the tip actuation mechanism in a plane extending through the longitudinal axis of the body effects motion of the at least one movable tip with respect to the other tip in the same plane. The distal end of the body of the instrument is adapted to be inserted into a patient during the laparoscopy.

8 Claims, 7 Drawing Sheets

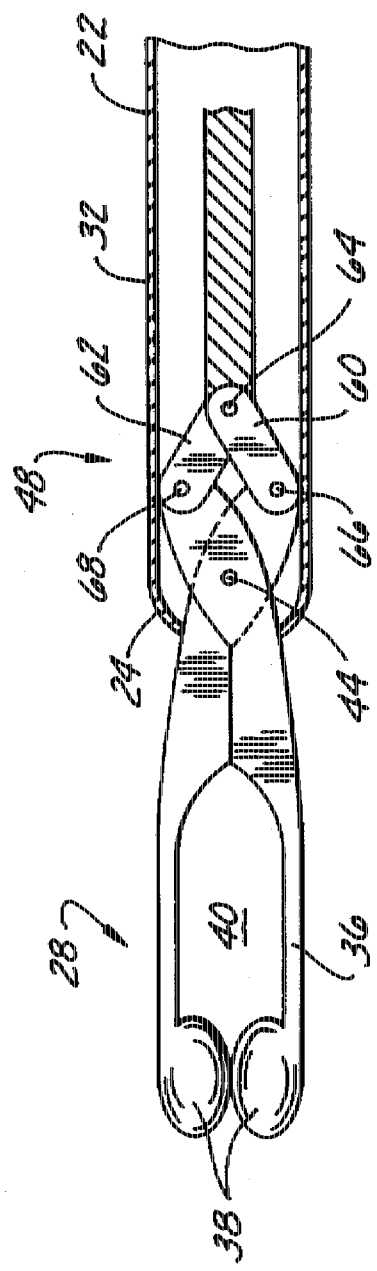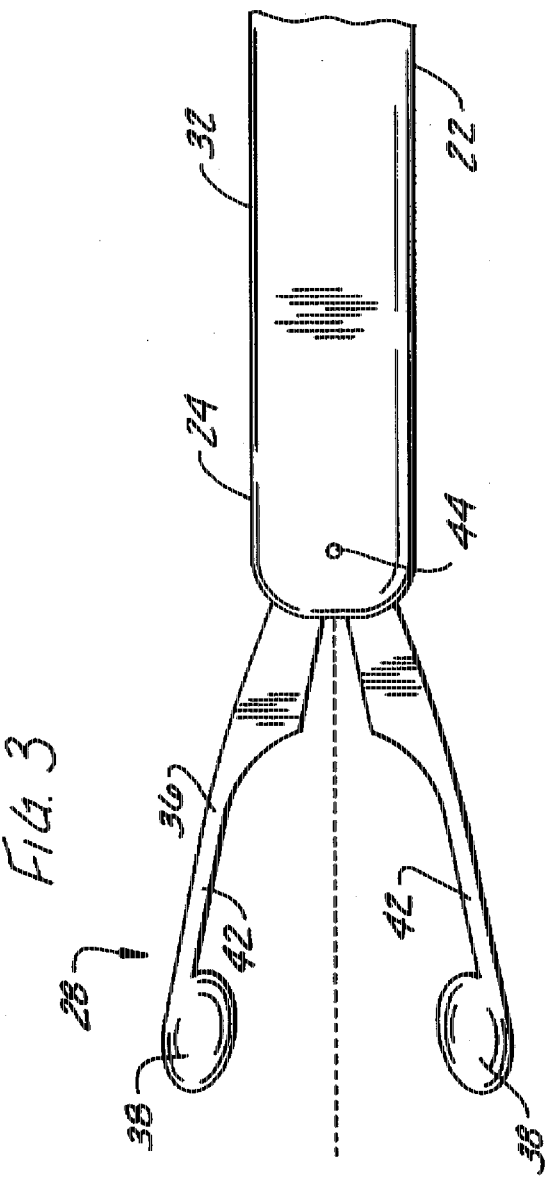

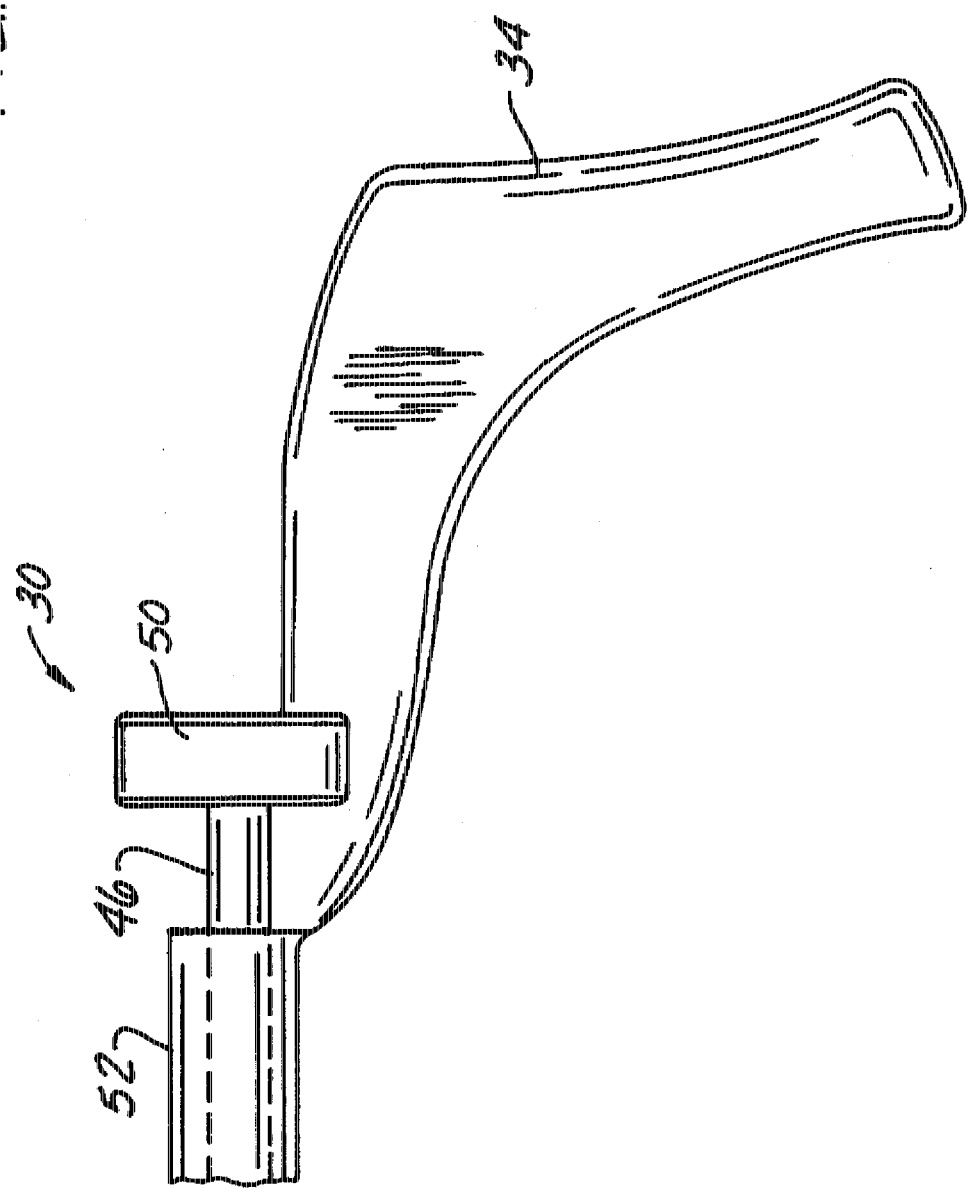

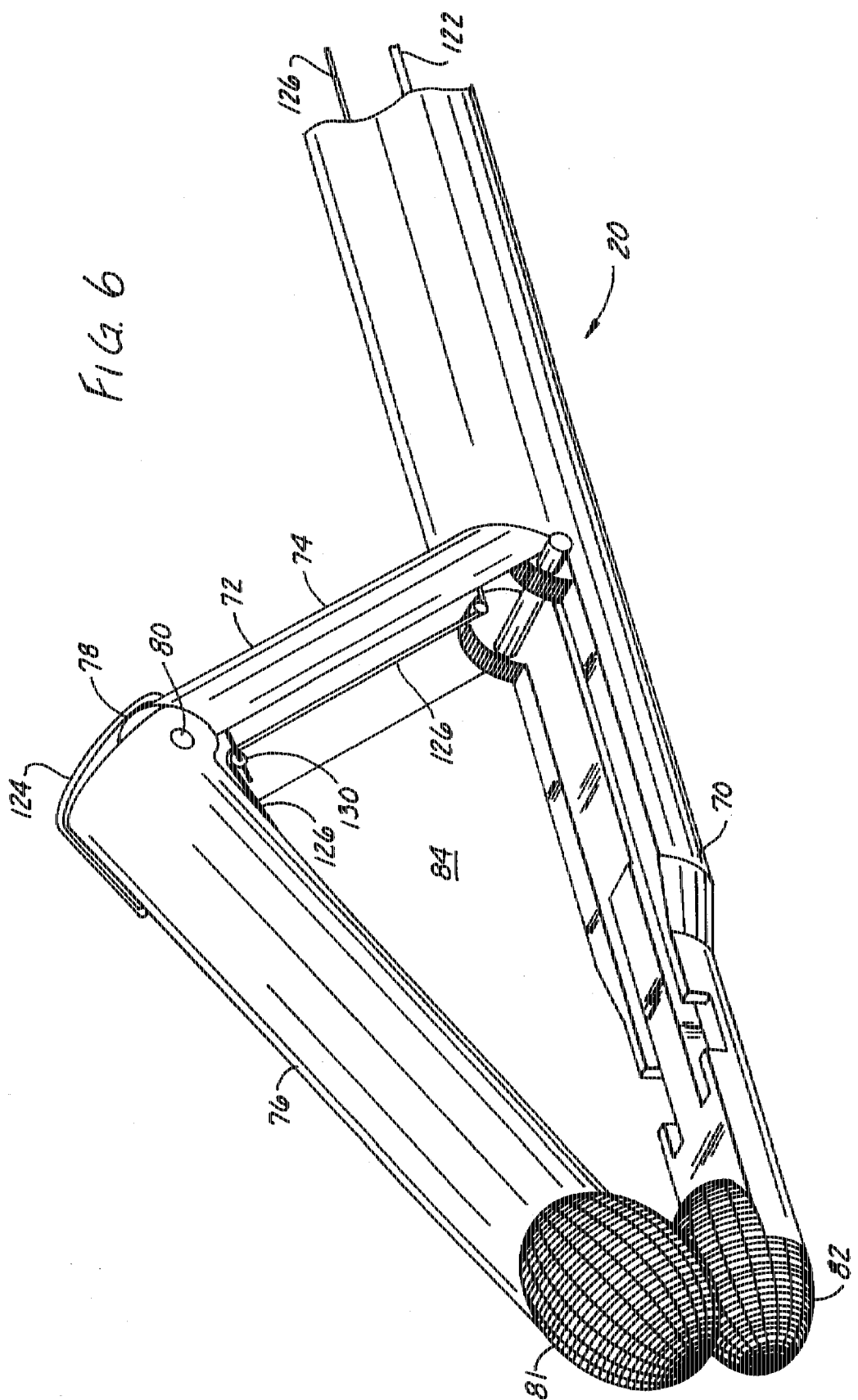

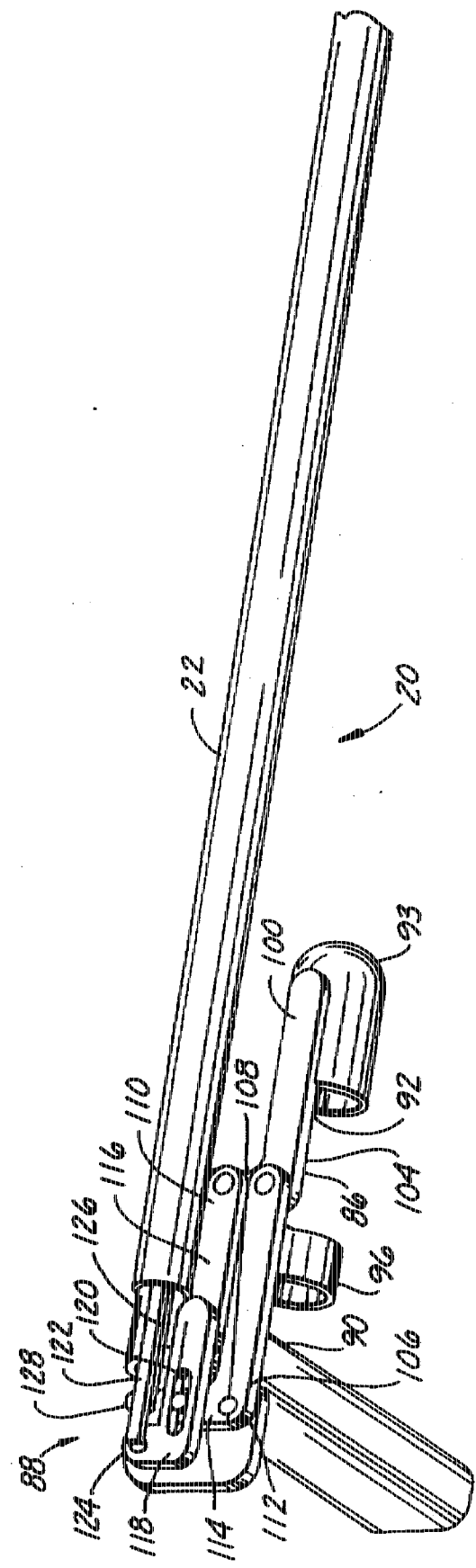

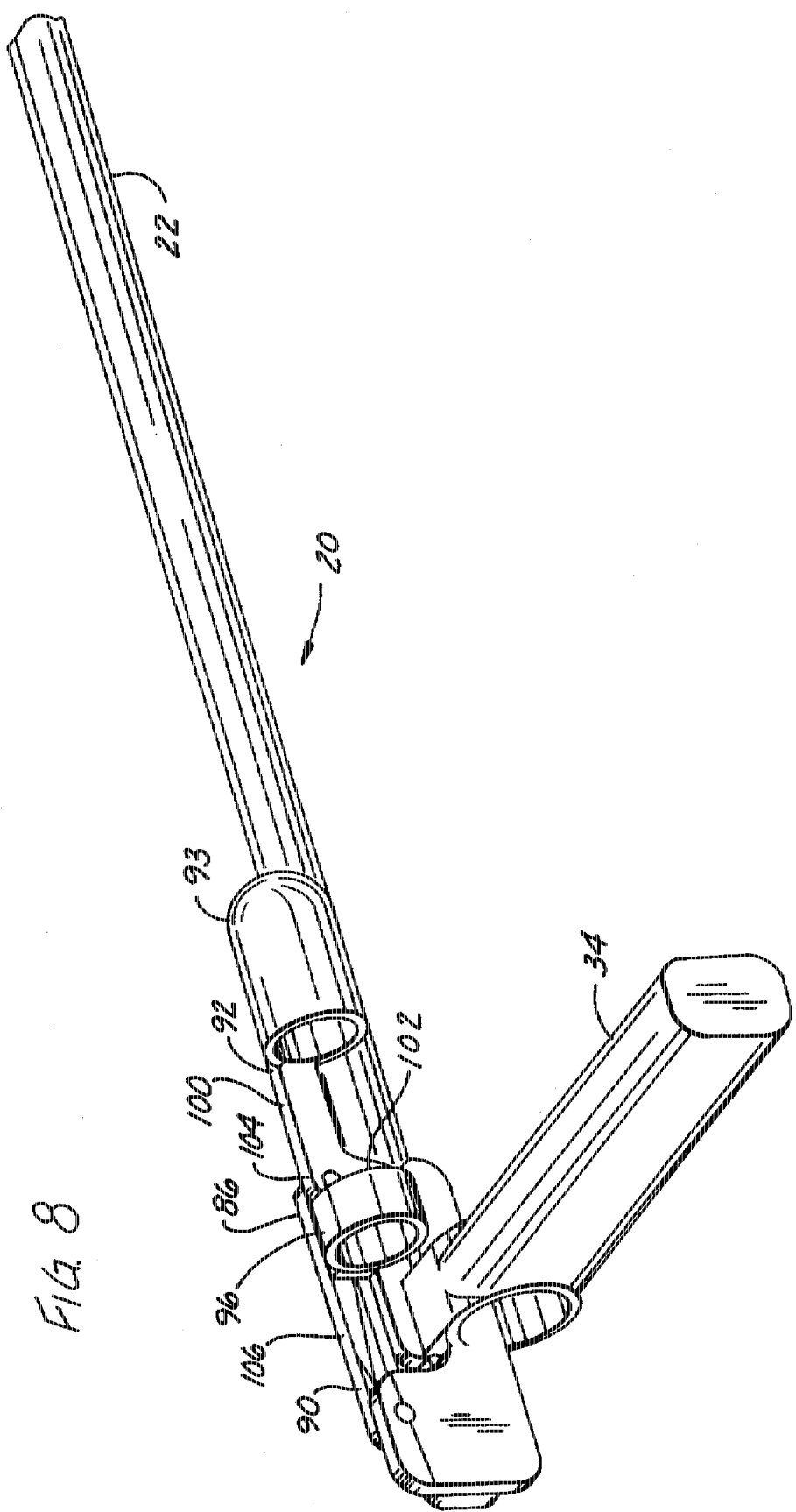

FINGERLIKE MEDICAL INSTRUMENTS FOR USE IN LAPAROSCOPIC PROCEDURES

This is a division of application Ser. No. 08/434,944, filed May 4, 1995 now pending.

BACKGROUND OF THE INVENTION

The present invention relates to medical instruments and, more particularly, medical instruments for use in a laparoscopy.

Instruments used to grasp, hold and/or compress tissue, body parts or surgical substances—such as forceps or clamps—are well-known for use in open surgical procedures. In a laparoscopy, however, these medical-instruments must be inserted through a slender cylindrical cannula—or trocar—to access the patient's abdominal cavity. The instruments designed for open surgeries are not sufficiently slender to pass through the trocar and are thus ill-suited for laparoscopic procedures.

Forceps and other medical instruments have been recently developed for use in a laparoscopy and include an elongate body that is extendable through a trocar into the patient and tips that are narrower than the elongate body. These instruments typically manipulate the tips from the proximal end thereof (i.e., the end nearest the surgeon) in the simplest fashion to translate motion to the distal end. For example, some laparoscopic instruments include an operating rod or sleeve that is pressed forwardly into a portion of the elongate body, which is held between the fingers of the surgeon, similar to a plunger on a conventional syringe to open and close the tips. Other laparoscopic instruments manipulate their tips by a pistol-like handle that is oriented at a 90° angle from the longitudinal axis of the body of the instrument.

While these instruments have proven to be generally satisfactory in opening and closing the tips, such actuating mechanisms do not provide the surgeon with the precise control over the grasping or clamping tip that is required in complex surgeries since these actuating mechanisms are not longitudinally aligned with the tips and the tips do not parallel the motion of the surgeon's fingers on the actuating mechanisms. The most important tools at the surgeon's disposal in an open surgery are his fingers, which enable the surgeon to feel around the abdominal cavity and move organs, etc. The need for an instrument that mimics the surgeon's fingers has become increasingly apparent with the expanding acceptance of laparoscopy for more complex abdominal operations, such as on the large intestine.

Further, the grasping tips on the present laparoscopic instruments pivot about a single pivot point, which may be problematical since tissue located near the pivot point can be pinched. Also, attempts to move or twist the intestine may result in a tear because of this simplistic pivot point and also because of the relatively sharp corners on the present laparoscopic instruments.

SUMMARY OF THE INVENTION

Among the several objects and features of the present invention may be noted the provision of a medical instrument for use in a laparoscopy; the provision of such a medical instrument that includes grasping tips, which internally parallel the external movement of the surgeon's fingers; the provision of such a medical instrument that places the surgeon's hand in longitudinal alignment with the tips; the provision of such a medical instrument that enables the instrument to be comfortably held by the surgeon; the provision of such a medical instrument that reduces the risk of internal injuries during the laparoscopic procedure; the provision of such a medical instrument that enables at least one of the tips to be articulable; and the provision of such a medical instrument that are either disposable or reusable.

Generally, a medical instrument of the present invention is designed for use in a laparoscopy and comprises a long, slender body, which has opposite ends distal and proximal relative to a person holding the instrument. The distal end of the body is adapted to be inserted into a patient during the laparoscopic procedure. The instrument further includes a pair of tips adjacent the distal end of the body, with at least one of the pair of tips movable with respect to the other of said tips, and tip actuation means movably connected at the proximal end of the body for actuating movement of the at least one movable tip. The tip actuation means is longitudinally aligned with the pair of tips and coplanar therewith such that motion of the tip actuation means in a plane extending through the longitudinal axis of the body effects motion of the at least one movable tip with respect to the other tip in the same plane.

Other objects and features will be in part apparent and in part pointed out hereinafter.

BRIEF DESCRIPTION OF THE DRAWINGS

FIG. 2 is a partial side elevational view of the distal end of the medical instrument with the tips in the closed position and a portion of the body cut-away to show the tip actuation mechanism;

FIG. 3 is a view similar to FIG. 2 with the tips in the open position;

FIG. 4 is a partial side elevational view of the handle grip of the instrument;

FIG. 6 is a similar view to FIG. 5 showing the articulated grasping tip in a closed position;

FIG. 7 is a partial perspective view of the tip actuation mechanism of the first alternative embodiment of the medical instrument; and FIG. 8 is a similar view to FIG. 7 showing the opposite side of the instrument.

Corresponding reference characters indicate corresponding parts throughout the several views of the drawings.

DETAILED DESCRIPTION OF THE PREFERRED EMBODIMENT

Figure 1:
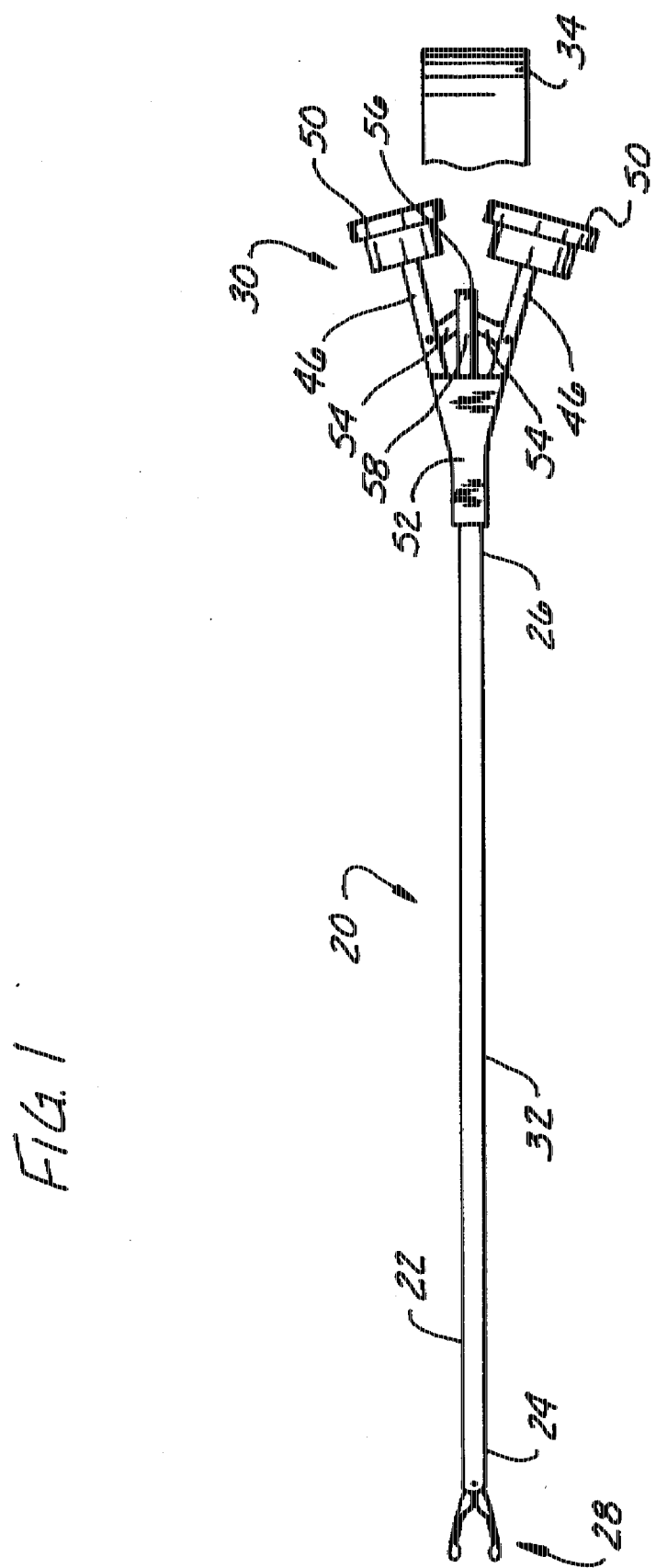
FIG. 1 is a plan view of the medical instrument of the present invention with the grasping tips in an open position.
Figure 5:
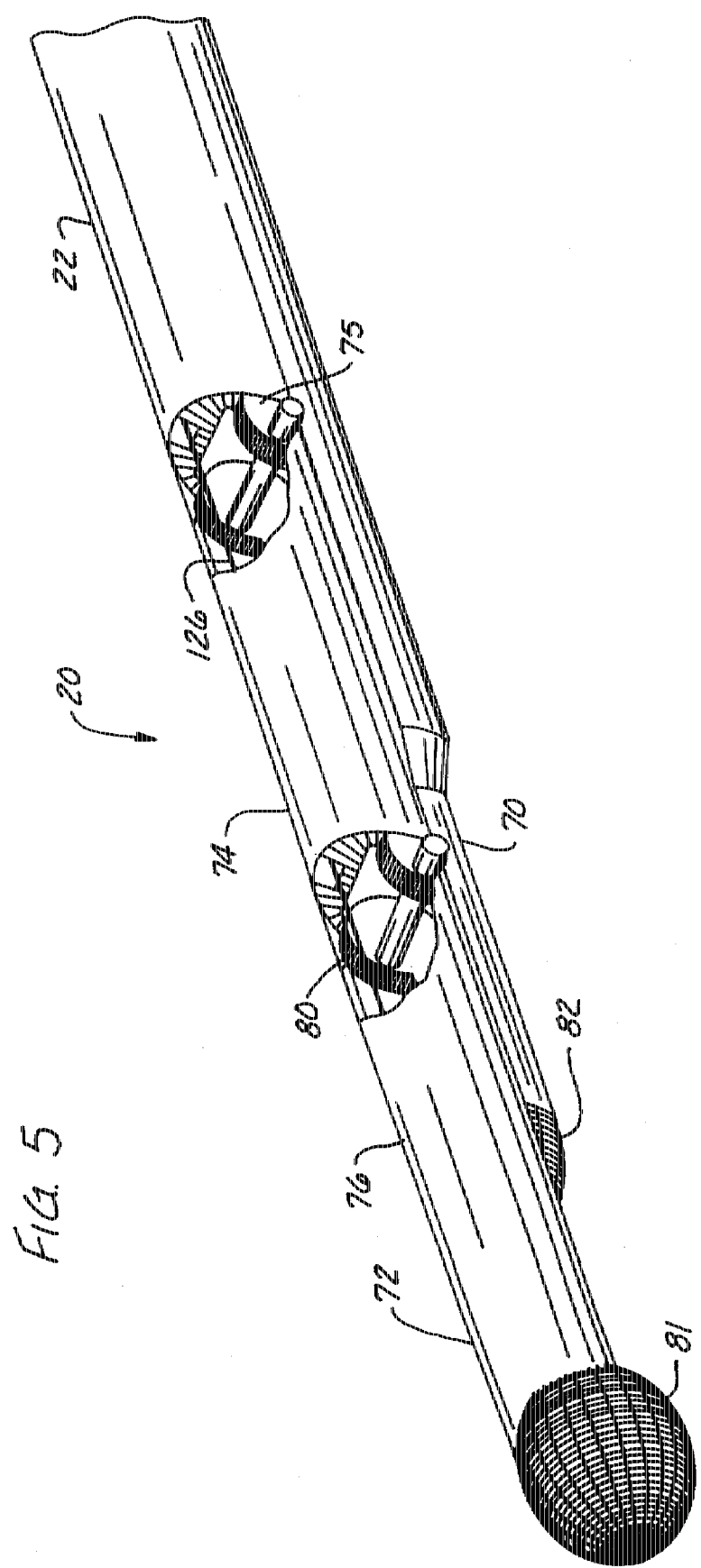
FIG. 5 is a partial perspective view of a first alternative embodiment of the medical instrument showing a jointed tip in the insert position, a portion of the body being cut-away to show the joints of the tip.

Referring now to the drawings, a medical instrument for use in a laparoscopy is indicated generally at 20. The instrument 20 comprises a long, slender body 22 having opposite ends, which are distal 24 and proximal 26 relative to a person (i.e., a surgeon) holding the instrument. The instrument 20 further includes a pair of tips, indicated generally at 28, adjacent the distal end 24 of the body 22, and tip actuation means, indicated generally at 30, movably connected at the proximal end of the body for actuating movement of the tips.

The body 22 of the instrument 24 comprises an elongate, cylindrical housing 32, preferably fabricated from stainless steel. The distal end 24 thereof is adapted to be inserted through a trocar and into a patient during the laparoscopy. For that purpose, the housing 32 is preferably approximately 14 inches in length and less than ½ inch in diameter. It will be understood that the housing 32 can be of any length and diameter without departing from the scope of the present invention. The body 22 includes a handle grip 34 mounted on the proximal end 26 of the instrument 20. The handle 34 is contoured to comfortably fit in the palm of the surgeon's hand while holding and manipulating the instrument during a laparoscopy. The handle 34 may include finger-receiving holes or grooves (not shown) to facilitate handling of the instrument 20. The handle 34 is affixed to the housing by screws so that the instrument may be disassembled for adjustment, sanitation, to enable replacement of a seal or other similar purpose. It will further be understood that the housing 34 can be made of a disposable plastic material without departing from the scope of the present invention.

The pair of tips 28, such as the grasping tips shown in the figures, extend from the distal end 24 of the tubular body 22 and are movable between an open position and a closed position (FIGS. 2 and 3). The grasping tips 28 include arms 36 that extend from the tubular body 22 and terminate in smooth, elliptically-shaped ends 38. These ends 38 preferably have a flattened bottom (not shown) that define a grasping surface. When the grasping tips 28 are in the closed position (FIG. 2), the elliptically-shaped ends 38 touch at the grasping surface to enable the surgeon to capture tissue therebetween. The arms 36 of the grasping tips 28 are likewise formed to have smooth, rounded edges to enable the instrument 20 to surround and slide over tissue with less chance of tearing the tissue. As shown in FIG. 2, the arms 36 of the grasping tips 28 further have a relatively thin frame near the elliptically-shaped ends 38. So configured, a gap 40 is created between the grasping tips 28 in the closed position. This gap 40 accommodates grasped tissue to protect the tissue against tearing or being pinched.

The tips 28 of the present invention can be configured in several embodiments. In each embodiment at least one of the pair of tips 28 is movable with respect to the other tip. In the first embodiment (FIGS. 1–3), the grasping tips 28 comprise two symmetrical tips 42 pivotally connected to a pin 44 adjacent the distal end 24 of the body 22. This pivot pin 44 allows the tips 42 to be selectively movable relative to one another in scissor-like motion between an open and closed position.

The grasping tips 42 are selectively opened and closed by symmetrical levers 46 (FIG. 1) pivotally connected to a pivot pin (not shown) adjacent the proximal end 26 of the body 22 and a linkage system, indicated generally at 48, translating the motion of the levers 46 at the proximal end of the instrument to motion of the tips 42 at the distal end 24 of the instrument. The levers 46 and linkage system 48 comprise the actuation means for the present embodiment. The levers 46 are longitudinally aligned and coplanar with the grasping tips 42 at the distal end 24 of the body 22 and include a control member 50 attached to the free end of each lever 46. Preferably, the control members 50 are shaped like thimbles to fully receive a fingertip of the surgeon. So configured, the tip actuation means 30 is fully responsive to movement of the surgeon's fingers in a plane extending through the longitudinal axis of the body of the instrument. The body further includes a fork sleeve 52, which receives and provides support for each lever 46 of the actuation means 30.

To translate the motion of the levers 46 to the tips 42, a linkage 54 is pivotally mounted on each lever at a point between the control member 50 and the pivot pin. Each linkage 54 is likewise pivotally connected to the proximal end of an actuating rod 56 at a pivot point 58. Upon relative movement of the levers 46 away from each other, the actuating rod 56 moves longitudinally from the proximal end 26 of the instrument 20 to the distal end 24 thus translating the pivoting motion of the levers into linear motion of the actuation rod, which allows the body 22 of the instrument to be slender. The actuating rod 56 extends from the proximal end 26 of the body 22 through the fork sleeve 52 and into the tubular housing 32 of the body 22 and to the grasping tips 42 at the distal end 24 of the body. The actuation rod 56 slides freely in the housing 32 of the instrument body 22. The fork sleeve 52 includes an O-ring assembly (not shown) to assure an airtight fit between the actuating rod 56 and the body 22 of the instrument 20, as required during a laparoscopy. The linear motion of the actuating rod 56 is transferred to pivoting motion of the grasping tips 42 at the distal end 26 of the body 22 through a pair of coupling link plates 60 and 62. These link plates 60, 62 are attached at one end to actuating rod 56 with pivot pin 64 and at their other end to grasping tips 42 through pivot pins 66 and 68, located on the proximal ends of the grasping tips. So configured, the linear motion of the actuating rod 56 is translated to pivoting movement of the grasping tips 42 to enable the tips 42 to parallel the motion of the surgeon's fingers.

It will be understood that many other types of linkage systems can be used to effect the pivoting of the grasping tips 42 without departing from the scope of the present invention.

An alternative embodiment of the instrument 20, which enables the surgeon to grasp larger body organs—such as the large intestine—is shown in FIGS. 5–8. In this embodiment, a non-pivoting or fixed tip 70 is opposed by a movable, jointed tip 72. In the illustrated embodiment, the tips 70, 72 are grasping tips. The movable grasping tip 72 includes a proximal phalange 74 pivotally mounted on the body 22 adjacent its distal end 24 through a hinge joint 75 and a distal phalange 76 pivotally mounted on the free end 78 of the proximal phalange through a hinge joint 80. In this embodiment, the grasping tips 70, 72 are movable between an insert position, a closed position and an open position. In the insert position (FIG. 5), the movable grasping tip 72 lies flat against the nonpivoting grasping tip 70 and the elliptically-shaped end 81 of the movable tip extends longitudinally beyond the elliptically-shaped end 82 of the fixed tip. In this position, the body 22 of the instrument 20 is extendable through a trocar to insert it inside the abdominal cavity. In the closed position, the proximal phalange 74 is pivoted to an approximately 60° angle and the distal phalange 76 is pivoted downwardly until both elliptically shaped ends 80, 82 are in contact. In this position, a substantial gap 84 is formed between the movable and fixed tips 72, 70, respectively, through which the large intestine or other body part or tissue can extend and be manipulated. In the open position, the proximal phalange 74 and the distal phalange 76 extend away from the non-pivoting grasping tip 70 to enable the tips to surround tissue.

A movable, jointed lever 86, comprising the tip actuation means for this embodiment, controls the movement of the movable grasping tip 72 through a linkage system, generally indicated at 88. The lever 86 is coplanar and longitudinally aligned with the movable grasping tip 72 and includes a proximal lever portion 90 and a distal lever portion 92 pivotally mounted on the proximal lever portion. The lever 86 includes a control member 93 attached at the distal end 94 of the lever and a clip 96 mounted on the proximal lever portion 90 to receive the surgeon's finger. Preferably, the control member 93 is shaped like a thimble to fully receive a fingertip of the surgeon. So configured, the tip actuation means is fully responsive to movement of the surgeon's fingers in a plane extending through the longitudinal axis of the body of the instrument.

Movement of the lever 86 in this plane is translated to corresponding movement of each segment of the movable grasping tip 72 in the same plane through a parallelogram linkage 98 (FIG. 7). The distal lever portion 92 includes a first member 100 having the fingertip-receiving control member 93 mounted thereon at one end and a second member 102 fixedly attached to or integral with the first member at one of its ends and extending perpendicular therefrom. The end 104 of the first member 100 opposite the finger-receiving control member 93 is pivotally connected to a first linkage 106 and the free end 108 of the second member 102 is pivotally connected to a second linkage 110. The end 112 of the first linkage 106 opposite its connection the first member 100 is pivotally mounted to a third linkage 114. The first, second and third linkages, 106, 110 and 114, respectively, comprise the proximal lever portion 90 of the lever 86. The second linkage 110 is generally L-shaped and includes a first section 116 extending from the second member 102 of the distal lever portion 92 and a second section 118 fixedly attached or integral with the first section and extending perpendicularly therefrom. The second linkage 110 includes a groove or channel 120 wherein the third linkage 114 is slidably received (FIG. 7). So formed, the linkage of the lever forms a parallelogram.

An actuating rod 122 effects movement of the proximal phalange 74 of the movable grasping tip 72. The actuating rod 122 is pivotally mounted on the free end 124 of the second section 118 of the second linkage to translate the pivoting motion of the proximal lever 90 into linear movement of the actuating rod. The actuating rod 122 extends through the housing 32 of the body 22 and is pivotally mounted by a hinge pin (not shown) on the proximal phalange 74. Since the actuating rod 122 extends through the body 32, this pivot pin connection is necessarily interior of the hinge pin connection between the proximal phalange 74 and the housing 32. As such, the linear movement of the actuating rod 122 effects pivoting of the proximal phalange 74 of the movable grasping tip 72 away from the non-pivoting grasping tip 70.

The distal phalange 76 of the movable grasping tip 72 is biased to an extended position (i.e. colinear with the proximal phalange) by a spring 124 mounted at one end on the exterior surface of the proximal phalange 74 and on the other end to the exterior surface of the distal phalange. The distal phalange 76 is prevented from extending beyond the longitudinal axis of the proximal phalange by a stop (not shown). The distal phalange 76 is controlled by a cable 126, which at the proximal end 26 of the body 22 is connected to the free end 128 of the third linkage 114 and at the distal end 24 of the instrument's body 22 extends through a series of pulleys 130 to the distal phalange of the movable grasping tip 72. The parallelogram linkage describe heretofore transforms the movement of the distal lever portion 92 away from the longitudinal axis of the proximal lever portion 90 into linear movement of the cable 126 from the distal end 24 of the body 22 towards the proximal end 26. This linear motion causes the distal phalange 76, which is spring-biased in the open, extended position, to be pivoted downwardly.

During a laparoscopy, the instrument 20 of the present invention is inserted into the abdominal cavity of the patient through a trocar. For this to be accomplished, the tips 28 of the instrument must be in the closed position or, for the alternative embodiment, the insert position. In the first embodiment, this is accomplished by the surgeon grasping the instrument by the handle grip 34 and inserting their thumb and forefinger in the control members 50 and moving the control members 50 towards one another until they touch. The linkage system translates this motion to the tips 42 and causes the tips to likewise close. In the alternative embodiment, the surgeon grips the handle and inserts his finger in the control member 93 and into the control clip 94. The control lever 86 is simply moved by the surgeon to lie flat against or parallel to the body 22 of the instrument 20, which causes the movable, jointed tip 72 to lie flat against the non-pivoting tip 70. The instrument 20 is then inserted through the trocar and into the abdominal cavity of the patient. With the distal end 24 of the instrument 20 positioned internally, the tips 28 of the instrument can be selectively opened and closed, as desired, by manipulating the tip actuating mechanism 30 for each embodiment as described above. For both embodiments, the plane of movement of the control levers is aligned with the plane of movement of the tips and the control levers are longitudinally aligned with the tips. The surgeon is thus constantly aware of the orientation and relative location of the jaws, even when not in view.

It is envisioned that the instrument 20 can have numerous different tips 28 (i.e., forceps, cutting tips, etc.) interchangeably mountable on the instrument of the present invention through a male and female interconnection at the tips. It is to be understood that the instrument of the present invention may include a laser fiber or irrigation/suction catheter extending through the body of the instrument without departing from the scope of the present invention.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A medical instrument for use in a laparoscopy, the instrument comprising, a long, slender body having opposite ends which are distal and proximal relative to a person holding the instrument, the distal end of the body being adapted to be inserted into a patient during the laparoscopy, first and second tips adjacent the distal end of the body, the first tip being jointed for movement with respect to the second tip along the longitudinal axis of the body, each tip having a distal free end, and tip actuation means movably connected at the proximal end of the body for actuating movement of the first tip, the tip actuation means being longitudinally aligned with said tips and coplanar therewith whereby motion of the tip actuation means in a plane extending through the longitudinal axis of the body effects motion of the first tip with respect to the second tip in the same plane, said first tip being operable between a first insert position in which the distal end of the first tip extends longitudinally beyond the distal end of the second tip and the first tip lays generally flat against the second tip, and a second closed position in which the distal end of the first and second tips are in contact with one another.

2. The medical instrument as set forth in claim 1 wherein the tip actuation means further effects motion of the first tip with respect to the other of said grasping tips along the longitudinal axis of the body.

3. The medical instrument as set forth in claim 2 wherein said second tip is fixed and the first and second tips define an opening as positioned with the distal free end of the first tip in contact with the distal free end of the fixed tip.

4. The medical instrument as set forth in claim 1 wherein the first tip includes more than one joint.

5. The medical instrument as set forth in claim 1 wherein the tip actuation means comprises at least one tip control lever and a control member mounted on each of the at least one tip control lever.

6. The medical instrument as set forth in claim 5 wherein the tip actuation means further comprises a grip assembly for facilitating the handling of the instrument by the operator.

7. The medical instrument as set forth in claim 5 wherein the at least one tip control lever includes a proximal phalange pivotally connected to the body of the instrument for movement in the plane extending through the longitudinal axis of the body, a distal phalange pivotally connected to the distal end of the proximal phalange for movement in the plane extending through the longitudinal axis of the body, and wherein the control member includes a thimble-shaped member mounted on the distal phalange for receiving the fingertip of the surgeon and a control ring mounted on the proximal phalange whereby movement by the surgeon's finger as properly positioned on the tip control lever in the thimble-shaped member and through the control ring effects like movement of the first tip at the distal end of the body.

8. The medical instrument as set forth in claim 5 wherein the control member is a thimble-shaped control member adapted to receive the operator's fingertip.

\* \* \* \* \*